United States Patent [19]
Miller et al.

[11] Patent Number: 5,168,067
[45] Date of Patent: Dec. 1, 1992

[54] METHOD AND KIT FOR SCREENING FOR APOLIPOPROTEIN B OR CALCULATED LDL CHOLESTEROL

[76] Inventors: Michael A. Miller, 5322 Medical Dr. #5202, San Antonio, Tex. 78240; Raymond G. Troxler, 10318 Willowick, San Antonio, Tex. 78217

[21] Appl. No.: 528,995

[22] Filed: May 25, 1990

[51] Int. Cl.⁵ .................. G01N 31/02; G01N 33/92
[52] U.S. Cl. .................................. 436/71; 422/61; 436/165; 436/181
[58] Field of Search ............... 422/61; 436/70, 69, 436/71, 165, 177, 181

[56] References Cited

U.S. PATENT DOCUMENTS

| | | | |
|---|---|---|---|
| 3,873,433 | 3/1991 | Seidel et al. | 201/180 E |
| 4,045,175 | 8/1977 | Weber | 436/70 |
| 4,128,400 | 12/1978 | Muhlbock et al. | 422/101 |
| 4,188,188 | 2/1980 | Willner et al. | 436/71 |
| 4,210,557 | 7/1980 | Handshuh | 252/408 |
| 4,211,530 | 7/1980 | Goverde et al. | 23/230 B |
| 4,226,713 | 10/1980 | Goldberg | 23/230 B |
| 4,272,478 | 6/1981 | Vihko | 422/57 |
| 4,425,438 | 1/1984 | Bauman et al. | 436/527 |
| 4,486,531 | 12/1984 | Ziegenhorn et al. | 435/19 |
| 4,521,519 | 6/1985 | Draeger et al. | 436/17 |
| 4,746,605 | 5/1988 | Kerscher et al. | 435/7 |
| 4,923,439 | 5/1990 | Seidel et al. | 436/71 X |

FOREIGN PATENT DOCUMENTS 0028274  5/1981  European Pat. Off. ............. 436/70

OTHER PUBLICATIONS

Lab. Med., 1983, Lehmann, C. A. et al., 14(12):782-784.
Ann. N.Y. Acad. Sci, 1985, Naito, H. K., 454:230-238.
Clin. Chem., 1987, Maciejko, J. J. et al. 33(11):2065-2069.

Primary Examiner—Robert J. Hill, Jr.
Attorney, Agent, or Firm—Fulbright & Jaworski

[57] ABSTRACT

A method and apparatus for biochemical screening of coronary risk in humans utilizing the steps of obtaining a blood specimen and treating the serum with a proportionate volume of a VLDL/LDL (very low density lipopropteins/low density lioproteins) precipitating reagent, preferably the precipitating agent being encapsulated. The treatment of the serum is accomplished by the use of a tube, preferably a small bore microcapillary tube, having the precipitating reagent affixed to the inside of the tube for reaction with the serum. After reaction, a VLDL/LDL precipitate column is formed and measured. The measured column is compared to a correlation chart of VLDL/LDL column heights to assay amounts of apolipoprotein B.

17 Claims, 3 Drawing Sheets

METHOD AND KIT FOR SCREENING FOR APOLIPOPROTEIN B OR CALCULATED LDL CHOLESTEROL

BACKGROUND OF THE INVENTION

The present invention relates to a method and apparatus for screening for serum apolipoproteins as a biochemical indicator of coronary risk.

The association between elevated levels of serum cholesterol and heart disease has become one of the most cognizant risk factors in adult populations. Recent studies have shown that one in five adults die of coronary heart disease as a direct result of elevated serum cholesterol levels, and one in three is at risk of the disease. However, early screening of patients for this health risk is not routinely performed by physicians unless specifically requested by the patient. This is due in part to reliance on the patient's family health history as an indicator of negative risk factor in cardiovascular disease and the expense and inconvenience of the testing procedure. Often the family physician does not have a convenient test apparatus that can be routinely used in the office for the determination of cholesterol and is therefore dependent on an analysis by an outside clinical laboratory to provide the data. In addition, variations exist in the screening procedures currently used by clinical laboratories to determine serum cholesterol and many procedures are expensive to the patient, time-consuming, and are prone to large variability which may lead to errors in diagnosis and treatment.

Numerous investigations have demonstrated an inverse correlation between heart disease and plasma levels of high density lipoprotein (HDL), a carrier (vehicle) of cholesterol. Specifically, elevated levels of HDL cholesterol have been associated with lower incidence of heart disease. Other vehicles of cholesterol transport are defined in terms of their hydrated densities. These include very low density lipoprotein (VLDL) $d < 1.006$ g/ml, low density lipoprotein (LDL) $d = 1.006-1.063$ g/ml, and HDL $d = 1.063-1.21$/g/ml.

One procedure commonly used to determine HDL cholesterol involves the precipitation of VLDL and LDL followed by centrifugation. The supernatant, which contains HDL-associated cholesterol, is then chemically or enzymatically assayed for cholesterol.

Several clinical studies suggest that direct measurement of LDL precipitate is a better indicator of the risk for coronary heart disease than nonspecific measurement of HDL cholesterol. In one procedure known in the art, VLDL and LDL are precipitated from serum, the mixture is centrifuged, and the volume of the precipitate is measured. Lehmann et al, *Lab. Med.*, 14:782, (1983). This volume can be directly related to the concentrations of VLDL and LDL. This procedure also enables one to determine the concentration of total cholesterol plus triglycerides as a screening test for hyperlipidemia. However, this method of predicting heart disease or the predisposition therefore is too imprecise for this procedure to serve as a mass screening program for large numbers of subject children and adults. This procedure does not predict the sum of cholesterol and triglyceride in a linear fashion. In addition, this procedure has been only performed on blood samples obtained by venous puncture because of the large blood volume required. Utilization of blood from a finger-stick source does not provide a sufficient volume of blood necessary to perform currently available analyses.

While far less blood can be obtained from finger-stick sampling of an individual than can be obtained from venous sampling, experience indicates that finger-stick blood sampling is much better tolerated and accepted by a subject than is venous sampling. Thus, the ability to use blood from finger-stick samples for assays of blood components increases the participation rate of subjects, and particularly children, in mass screening programs.

Further, it is known that some individuals with coronary heart disease have normal cholesterol levels. This fact must be kept in mind when developing a method and device for screening large numbers of people. A possible explanation is that these "normocholesterolemic" individuals have abnormalities in cholesterol metabolism not detected by measuring the total cholesterol level.

The importance of apolipoproteins and the increased interest in the measurement of these proteins stems from the specific function each class of apolipoprotein has in the mechanism of lipoprotein metabolism and their relationship to a diseased state. In LDL metabolism, cholesterol is delivered to peripheral cells by LDL receptor sites located on the cell membrane. Elevated levels of intracellular cholesterol cause suppression of LDL receptor activity and subsequent accumulation of atherogenic LDL. Apo-B is the structural entity of LDL that is responsible for LDL receptor recognition by the peripheral cells. Whereas LDL particles are heterogeneous in terms of size and composition, each LDL particle has one molecule of Apo-B per particle. Thus, atherogenicity is best measured by the Apo-B component rather than by the varying number of cholesterol components.

Hyperapo-B-lipoproteinemia, detectable even in the pediatric age group, as well as in adults, is very prevalent in patients with coronary artery disease. In men, low-density lipoprotein cholesterol and apolipoprotein B levels correlated best with severity of the disease; in women the best discriminators were LDL and intermediate density lipoprotein (IDL) triglycerides, LDL cholesterol, and LDL/apolipoprotein B.

In hyperapolipoprotein B there is an increased number of atherogenic LDL particles in the blood that have an altered chemical composition: the core is depleted of cholesterol ester, and relatively enriched with apolipoprotein B. Increased numbers of smaller denser LDL particles result. Tests which measure only total cholesterol or LDL cholesterol underestimate the number of atherogenic LDL particles. In some families increased levels of apolipoprotein B may indicate the presence of lipoprotein phenotypes IV, IIa, and IIB, indicative of familial combined hyperlipidemia, that is so prevalent in survivors of myocardial infarctions.

Using cholesterol levels alone to screen asymptomatic adults for risk of coronary artery disease will give some individuals false assurance that they are at a low risk for a heart attack if these individuals have a normal cholesterol and elevated levels of LDL, low levels of HDL, or elevated levels of apolipoprotein B. Primarily due to cost, it is not usually recommended that mass screening programs measure triglycerides, HDL cholesterol, or LDL cholesterol.

Correlation of Apo-B blood levels and the severity of clinically verified coronary artery disease in patients has been evaluated by Naito. *Ann. NY Acad. Sci.* 454:230-238, (1985). Subjects of this study were divided into four categories: 1) asymptomatic patients not undergoing coronary angiography; 2) those with clinically nonsignificant coronary artery disease; 3) those with clinically significant coronary artery disease; and 4) those with severe coronary artery disease. Clinical verification of diseased states in each category was accomplished by coronary angiography. The presence or absence of coronary artery disease was assessed on the basis of the degree of stenosis within any segment of the arterial tree. Serum Apo-B levels were determined for ten subjects in each category by an immunochemical assay and the data obtained therefrom are set forth in Table 1.

TABLE 1

Relation of Apo-B Concentrations (mg/dl) to the Progression of Coronary Heart Disease (CHD).

| | Normal Asymptomatic Subjects (N = 10) Mean + SD | No Significant CHD[a] (N = 10) Mean + SD | Significant CHD[b] (N = 10) Mean + SD | Severe CHD[c] (N = 10) Mean + SD |
|---|---|---|---|---|
| Apo B | 107 ± 25 | 116 ± 24 | 129 ± 20 | 137 ± 26 |

[a]1-50% stenosis in at least one coronary arterial segment.
[b]51-99% stenosis in at least one coronary arterial segment.
[c]100% stenosis in at least one coronary arterial segment.

It is evident that in order to avoid false negative reports, effective screening of children and adults for the development of premature heart disease must include the measurement of apolipoprotein B. However, due to the high cost of currently available methods for measurement of apolipoprotein B, they are impractical for use as mass screening tests.

What was needed was a rapid, inexpensive, accurate and reliable method to predict individuals with high coronary risk. What was also needed was an effective method for predicting coronary risk in an individual which could be used in mass screening tests.

SUMMARY OF THE INVENTION

The present invention provides a rapid, inexpensive and accurate method for predicting coronary risk in an individual. The present invention further provides a method of assessing coronary risk in an individual utilizing capillary blood samples. The present invention also provides a self contained kit for assaying coronary risk by the measurement of Apo-B.

The present invention comprises a method for predicting coronary risk in a subject by correlating the volume of precipitated VLDL/LDL in a fixed serum volume with known levels of VLDL/LDL and further relating said VLDL/LDL levels with standard levels known to those skilled in the art to predict coronary disease risk.

The present invention comprises contacting a cell-free sample of blood with a precipitating agent in a calibrated tube, mixing said sample with said precipitating agent, centrifuging said mixture, determining the volume of said precipitate by reading from the calibration marks on said tube and correlating said precipitate volume with the total blood VLDL/LDL by comparison with the graph shown in FIG. 2.

In the method of the present invention, the precipitating agent is preloaded in the tubes. Preferably, the precipitating agent is encapsulated in microcapsules. The precipitating agent useful in the present invention is selected from the group consisting of a high molecular weight polyanion or a polyanion and a divalent cation. Preferably, said polyanion is selected from the group consisting of phosphotungstic acid, and sulfated polysaccharides. In practicing the present invention said sulfated polysaccharide may be selected from the group consisting of heparin, and dextran sulfate. The divalent cation useful in practicing the present invention may be selected from the group consisting of salts, preferably chloride salts, of magnesium, manganese and calcium.

In one embodiment of the present invention, a standard large bore microcapillary tube is used to collect blood from a finger-stick sample of the patient. One end is capped and the tube is immediately centrifuged to separate the red blood cells from the serum. The cap is removed and a second, calibrated, graduated, smaller bore microcapillary tube is introduced into the opening of the larger microcapillary tube. The serum from the larger tube is drawn up by capillary action to a reference line on the second smaller tube calibrated to ensure the appropriate amount of serum is drawn into the second microcapillary tube. The second tube is capped and placed on a rocker device. The inner lining of the second, smaller bore tube contains precipitating reagent attached to the inner surface by time-release microcapsules. After the precipitation is complete, the second smaller microcapillary tube is centrifuged and the height of the precipitate is recorded by reading the graduated calibrations (in units of volume) on the tube. The apolipoprotein B or LDL-cholesterol level of the patient is determined by comparing the height of the precipitate to a correlation graph which relates the volume of the precipitate to the concentration of apolipoprotein B or LDL-cholesterol in the serum.

Through the method and apparatus of the present invention, coronary risk can be correlated linearly with VLDL/LDL precipitates and the concentration of apolipoprotein B (Apo-B), the principal protein moiety of LDL. This has been verified by examining Apo-B in adolescents and adults by a currently available procedure (immunonephelometric assay) and by the use of the VLDL/LDL precipitation technique of the present invention. Tests of the present invention indicate that volume measurements of VLDL/LDL precipitates strongly correlated ($r^2=0.981$) with specifically assayed Apo-B.

DETAILED DESCRIPTION OF THE PREFERRED EMBODIMENT

Figures 1A, 1B, 1C:
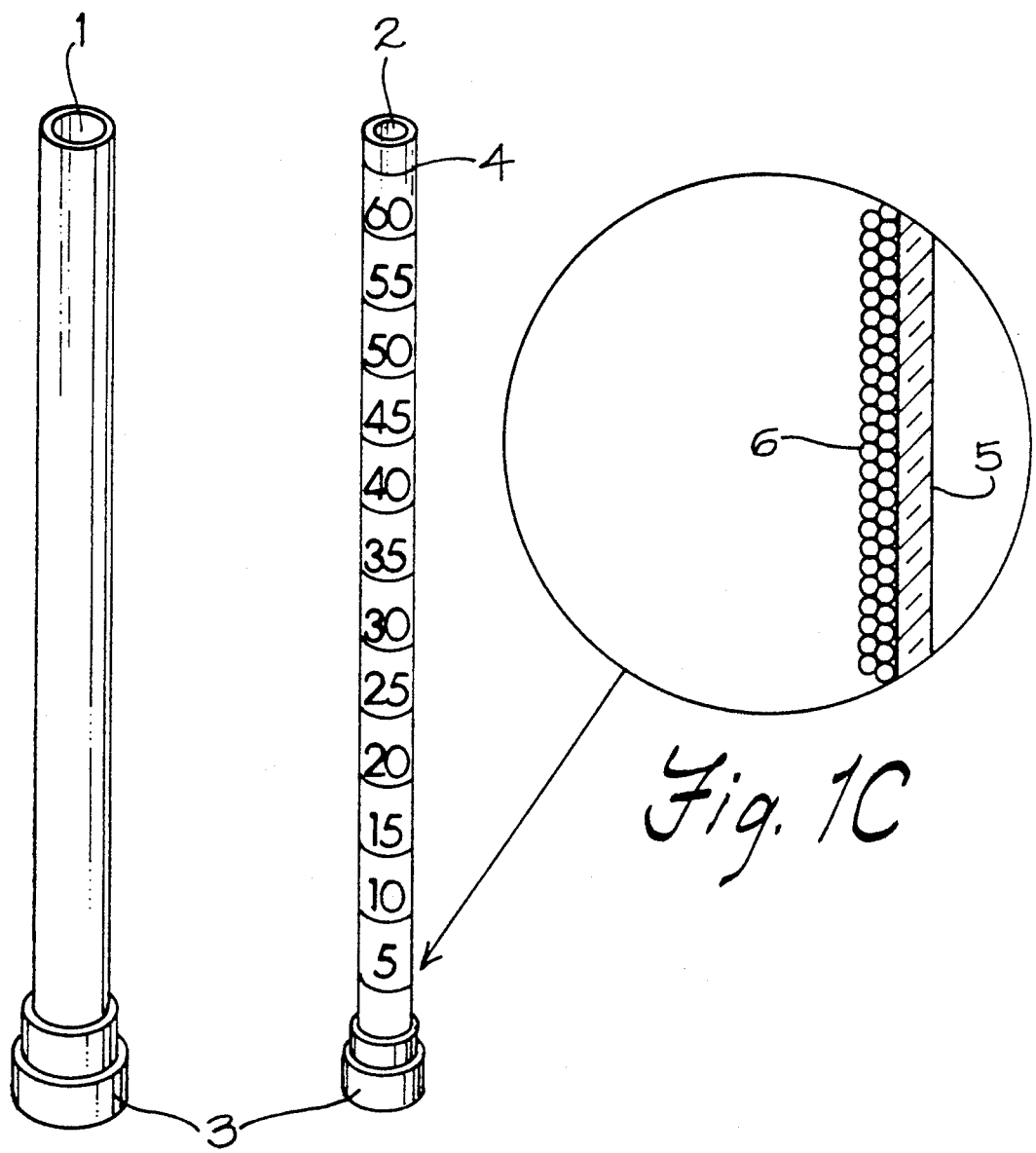
FIGS. 1A-C are schematic diagrams of the microcapillary devices used to determine VLDL/LDL precipitate column volumes.

The present invention comprises a method and a kit for the assessment of coronary risk assessment in an individual. The present invention being easy to use, rapid and reliable is suitable for use in a doctor's office and in small clinical laboratories. Unlike other methods for assessing coronary risk, large, expensive equipment is not required. The method of the present invention comprises collecting a blood sample from a subject, removing the red blood cells from said blood sample by centrifugation in a centrifuge, drawing a fixed volume sample of the serum into a microcapillary tube containing an agent which precipitates VLDL and LDL, precipitating said VLDL and LDL and determining the amount of VLDL and LDL in the blood sample by correlating the volume of the precipitate with a standard chart as shown on FIG. 2 and assessing the coronary risk in the individual.

Blood samples are drawn from subjects, who have preferably fasted for at least 12 hours. However, while the accuracy of the test is greater on fasted subjects, it will be obvious to one skilled in the art that the degree of fasting may be taken into consideration in analyzing the results and the test therefore may be performed on subjects who have fasted for less than, or longer than, twelve hours without deviating from the present invention. The blood may be drawn from venous puncture, arterial puncture or finger-sticks. Only a small volume of blood is needed to practice the present invention. Thus, it is sufficient if at least 20 $\mu$l of whole blood or 10 $\mu$l of serum is available for the VLDL/LDL precipitation procedure. Preferably, the blood sample is collected from a finger-stick in a first capillary tube having an internal volume of at least 20 $\mu$l. Regardless of the site of the blood sampling, the cellular components are removed from the sample by low speed centrifugation, at least 2 min. at 800×g. The procedures for separating cells from whole blood are well known to those of skill in the art.

A sample of the cell-free serum is drawn into a second tube. Said second tube contains an agent which precipitates VLDL and LDL but does not precipitate HDL.

The precipitating agent useful in practicing the present invention is selected from the group consisting of a high molecular weight polyanion and the combination of a polyanion and a divalent cation. Preferably, said polyanion is selected from the group consisting of phosphotungstic acid, and sulfated polysaccharides. In practicing the present invention said sulfated polysaccharide may be selected from the group consisting of heparin, and dextran sulfate. The divalent cation useful in practicing the present invention may be selected from the group consisting of salts, preferably chloride salts, of magnesium, manganese and calcium. Most preferably, the precipitating agent is 0.01M phosphotungstic acid and 0.128M NaOH in 0.4M magnesium chloride (pH adjusted to 7.4 with 1N HCl). Preferably, the ratio of the volume of precipitating agent used to the volume of sample is about one part precipitating agent to about five to eight parts sample. Most preferably, the ratio used to practice the present invention is one part precipitating agent to seven parts sample.

Preferably, the precipitating agent is encapsulated in polymer microcapsules of approximately 100 $\mu$m in diameter. Encapsulation procedures useful in practicing the present invention are known to those skilled in the art of microencapsulation. For instance, the procedure taught and disclosed in U.S. Pat. No. 3,389,194 (Somerville) may be used to encapsulate the precipitating agent.

Briefly, in the manufacture of small capsules useful in practicing the present invention, filler material is contained within a seamless film material (shell). A centrifugal extrusion device is used to manufacture the microcapsules. The device consists of an encapsulation head with two or more nozzles and concentric feed tubes which enter the head through a seal arrangement. The device is attached to a rotating shaft such that the direction of rotation is around its vertical axis. Shell and fill materials are pumped separately through a feed tube into the head and to the nozzles which consist of concentric orifices. As the head rotates, shell material flows through the outer orifice of the nozzle and fill material flows through the inner orifice of the nozzle, thereby creating a rod of filler material surrounded by a sheath of shell material. This extruded rod of material eventually breaks into individual capsules which are collected by appropriate means.

However, any other encapsulating procedure known to those in the art may be used as long as the encapsulated precipitating agent is capable of precipitating VLDL/LDL when contacted with a sample containing said compounds. The precipitating agent may also be directly bound to the inner walls of the calibrated assay tube as long as when so bound the precipitating agent is capable of precipitating VLDL/LDL when contacted with a sample containing said compounds without altering the sedimentation of the formed precipitate upon centrifugation.

EXAMPLE 1

Blood samples were drawn from fasting subjects and separated into duplicate samples. The blood samples were collected in standard blood collection test tubes by venous puncture and the serum was separated by procedures known to those of skill in the art. One of the duplicate samples from each subject is assayed using currently available immunonephelometric assay procedures to determine the level of apolipoprotein B (Apo-B) in the blood, Maciejko et al., *Clin. Chem* 33:2065 (1987). The second duplicate sample was processed by the method of the present invention to yield a VLDL/LDL precipitate volume. The second duplicate sample of serum was drawn into a test tube to which was added a proportionate volume of precipitating reagent (at a ratio of serum to reagent volume of 7:1). The precipitating reagent was 0.01M phosphotungstic acid and 0.128M NaOH in 0.4M magnesium chloride (pH adjusted to 7.4 with HCl). A portion of the duplicate sample was drawn into a capillary tube. The capillary tube was capped and vigorously agitated by a rocker device for approximately ten minutes. Once the reaction between the reagent and the serum was complete (approximately 10 min.), the capillary tube was placed in a centrifuge and spun at approximately 800×g for approximately six minutes to provide a VLDL/LDL precipitate column. It may be understood that centrifuging at a greater or lesser force level or for a different time period will yield a more or less compacted precipitate column; thus, appropriate variations may be made to the method of the present invention without departing from the spirit or scope of the invention.

Figure 2:
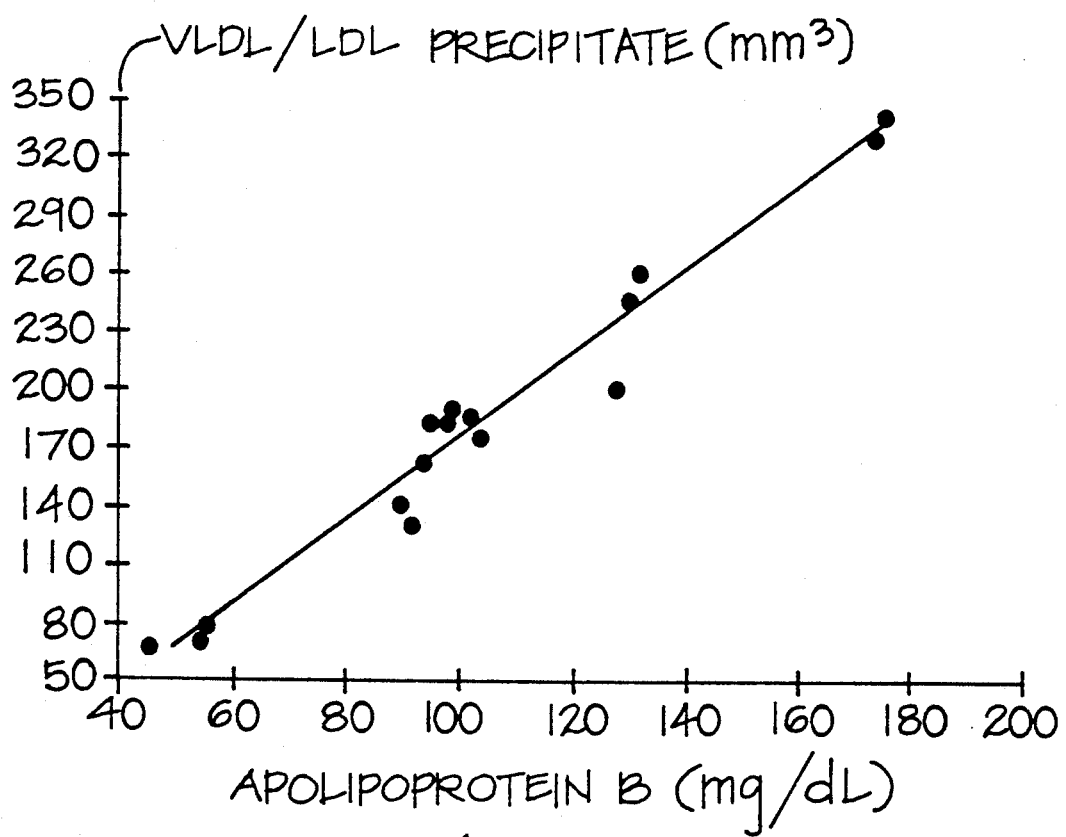
FIG. 2 is a graph of the relationship of VLDL/LDL precipitate column volume to amount of apolipoprotein B in a blood sample.

The correlation of VLDL/LDL precipitate column volumes measured by the precipitation method of the present invention in aliquot samples with amounts of apolipoprotein B determined by immunonephelometric assays on duplicate aliquot samples is shown in FIG. 2. The volume measurement of VLDL/LDL precipitate strongly correlated ($r^2 = 0.981$) with the Apo-B amounts determined by immunonephelometric assay.

Alternatively, the samples are obtained by the standard finger-stick method known to those in the art. The finger-stick samples are collected in standard large bore microcapillary tubes, such as, for example, the Sarstedt Microvet brand tube.

The capillary tube 1 is capped 3 and spun immediately in a centrifuge to separate the serum (FIG. 1A). A smaller bore capillary tube 2 having an outside diameter less than the inside diameter of the standard capillary tube 1 is then used to withdraw a specific volume (approximately 10 μl) of the serum into the smaller bore capillary tube 2 (FIG. 1B). The volume to be withdrawn is marked by a graduated level 4 on the outside of the small tube 2. In one embodiment the smaller bore tube 2 is preloaded with a proportionate volume of precipitating reagent (at a ratio of serum to reagent volume of 7:1). Alternatively, the precipitating reagent may be added after the serum. The precipitating reagent is preferably 0.01M phosphotungstic acid in 0.4M magnesium chloride (pH adjusted to 7.4 with HCl). Alternatively, the precipitating agent may be affixed to the inner surface of the small capillary tube 5 and preferably, is contained in time-released microcapsules 6 (such as that depicted in FIG. 1C).

The VLDL/LDL precipitation reaction is initiated upon withdrawal of the specific volume of serum from the test tube or larger, standard bore capillary tube 1 into the smaller bore tube 2. The smaller tube 2 is capped 3 and vigorously agitated by a rocker device for approximately ten minutes. The reaction is carried out as described above for samples collected from venous blood.

EXAMPLE 2

Determination of coronary risk in non-control subjects is assessed by the method of the present invention. A blood sample from a finger-stick of a subject is drawn into a standard microcapillary tube. This non-control sample is then capped and spun in a centrifuge to separate the serum in the same manner as was done with the control samples in Example 1. A measured volume of serum is withdrawn from the standard microcapillary tube into a smaller bore tube previously prepared with a proportionate volume of precipitating reagent (ratio of serum to reagent volume is 7:1), consisting of 0.01M phosphotungstic acid in 0.4M magnesium chloride (pH adjusted to 7.4 with HCl), affixed to the inner surface of the small capillary tube by time-released microcapsules, as described in Example 1. The smaller bore tube is capped and vigorously agitated by a rocker device until the reaction of the precipitation reagent with the serum sample is complete. The smaller bore tube is then centrifuged and spun at approximately 800×g for approximately six minutes to form a VLDL/LDL precipitate column. The column volume of the sample is then located on the y-axis of the graph shown on FIG. 2, and the correlation of the column height with the APO-B serum level is read on the x axis.

Alternatively, the column volume of the sample can be related to serum Apo-B level by applying a multiplication factor (mg/dl/mm$^3$) that is calculated from a control serum sample, and for which the concentration of Apo-B has been previously determined by a reference laboratory. The control serum sample is processed by the method of the present invention to yield a VLDL/LDL precipitate volume. A multiplication factor is derived from this measurement by dividing the known concentration of Apo-B (mg/dl) in the control by the resulting VLDL/LDL precipitate volume (mm$^3$), thus giving mg/dl of Apo-B per mm$^3$ of precipitate. As the linearity of the present invention has been demonstrated (FIG. 1), this multiplication factor can be applied to the resulting column volume of the sample to give mg/dl of Apo-B in sample.

EXAMPLE 3

Kits embodying the present invention can be prepared in various configurations to contain sufficient components to perform any number of sample analyses. A minimum test-kit suitable for one replicate Apo-B determination on one sample comprises:

2 large bore capillary tubes, preferably with caps;
1 small bore graduated capillary tube preferably with a cap;
2 additional small bore graduated tubes preferably with caps, each containing microcapsules of precipitating agent, preferably 0.01M phosphotungstic acid in 0.4M magnesium chloride (pH 7.4) prebonded to their inner surface (as illustrated in FIG. 1.);
2 sterile blood lancets; and
1 vial containing lyophilized control serum with a known amount of Apo-B (ranging from 50 to 150 mg/dL, preferably, 100.0 mg/dL).

The kit of the present invention may also contain sufficient distilled water to reconstitute the components or, alternatively, the user may supply its own distilled water.

In a most preferred embodiment the tubes have color coded caps. For instance, the 2 large bore capillary tubes may have red caps; the first small bore graduated capillary tube may have a blue cap; and the second two small bore graduated capillary tubes may have red caps. The use of the kit of the present invention is further described in Example 4 below.

EXAMPLE 4

The contents of the vial containing the control serum described in Example 3 are reconstituted by filling the vial with distilled water to the graduation mark. The vial is then stoppered and vigorously agitated until the contents are in solution.

The blue cap is removed from the small bore graduated capillary tube. Reconstituted control serum is drawn into the tube through capillary action by submerging the tip of the tube into the vial long enough so that the level of serum reaches the reference line marked on one end of the tube. One opening of the tube is then capped (blue cap) on the end opposite from the reference line. The capped tube is allowed to stand for 20 minutes to initiate the precipitation reaction. Subsequent to the precipitation reaction, the tube is centrifuged at 800×g for approxiamtely 6 minutes and the precipitate column volume is read directly from the graduation marks.

A response factor is calculated from the following formula:

$$R = \frac{\text{Known Apo-}B \text{ Concentration}}{\text{Column Volume}}$$

The red caps are removed from the large bore capillary tubes and are placed aside. Using a sterile blood lance, a finger-stick blood sample is obtained. Blood samples are drawn into each of the two large bore capillary tubes by submerging the tip of each tube into the sample. The tubes are then capped at one end and are subsequently centrifuged at least 2 min. at 800×g to separate serum (supernatant). Serum from these tubes is drawn into the remaining two small bore capillary tubes by introducing each small bore tube into the opening of each large bore tube. The small bore tubes are then capped as described above. After the precipitation reaction is complete (20 min.), the tubes are centrifuged as previously described to obtain a precipitate column. The precipitate column volume of each sample tube is related to serum Apo-B concentration by the following formula:

Apo-B Conc. = Average Sample Column Volume × R

EXAMPLE 5

Alternatively, a mass screening test-kit capable of multiple determination may be prepared. An example of such a mass screening test kit sufficient for Apo-B determinations on approximately 100 test samples comprises:
100 large bore capillary tubes with red caps;
10 small bore graduated capillary tubes with blue caps;
100 additional small bore graduated tubes with red caps, each containing microcapsules of precipitating agent prebound to their inner surface (as illustrated in FIG. 1.);
100 sterile blood lancets;
5 vials labeled LEVEL I containing lyophilized control serum with a known amount of Apo-B (ranging from 50-150 mg/dL, preferably 100 mg/dL); and
5 vials labeled LEVEL II containing lyophilized control serum with a known amount of Apo-B (ranging from 50-150 mg/dL, preferably 150 mg/dL).

Contents of mass screening test-kit are sufficient for 100 determinations of Apo-B.

EXAMPLE 6

Determination of Apo-B utilizing the test kit of Example 5 is performed in accordance with the procedure described in Example 4 with the exception that two response factors (R and RO are calculated from two serum controls (Level I and II) of known Apo-B concentration. The concentration of Apo-B in the sample is calculated by using the response factor whose precipitate column volume is nearest to that of the sample.

It is apparent that this variation in the method of the present invention may be utilized with any kit regardless of the number of test determinations the kit is prepared for. Alternatively, larger mass test kits need not contain the second control (LEVEL II) reference control serum. The entire test may be performed utilizing the single reference or control serum as in Example 4.

EXAMPLE 7

Figure 3:
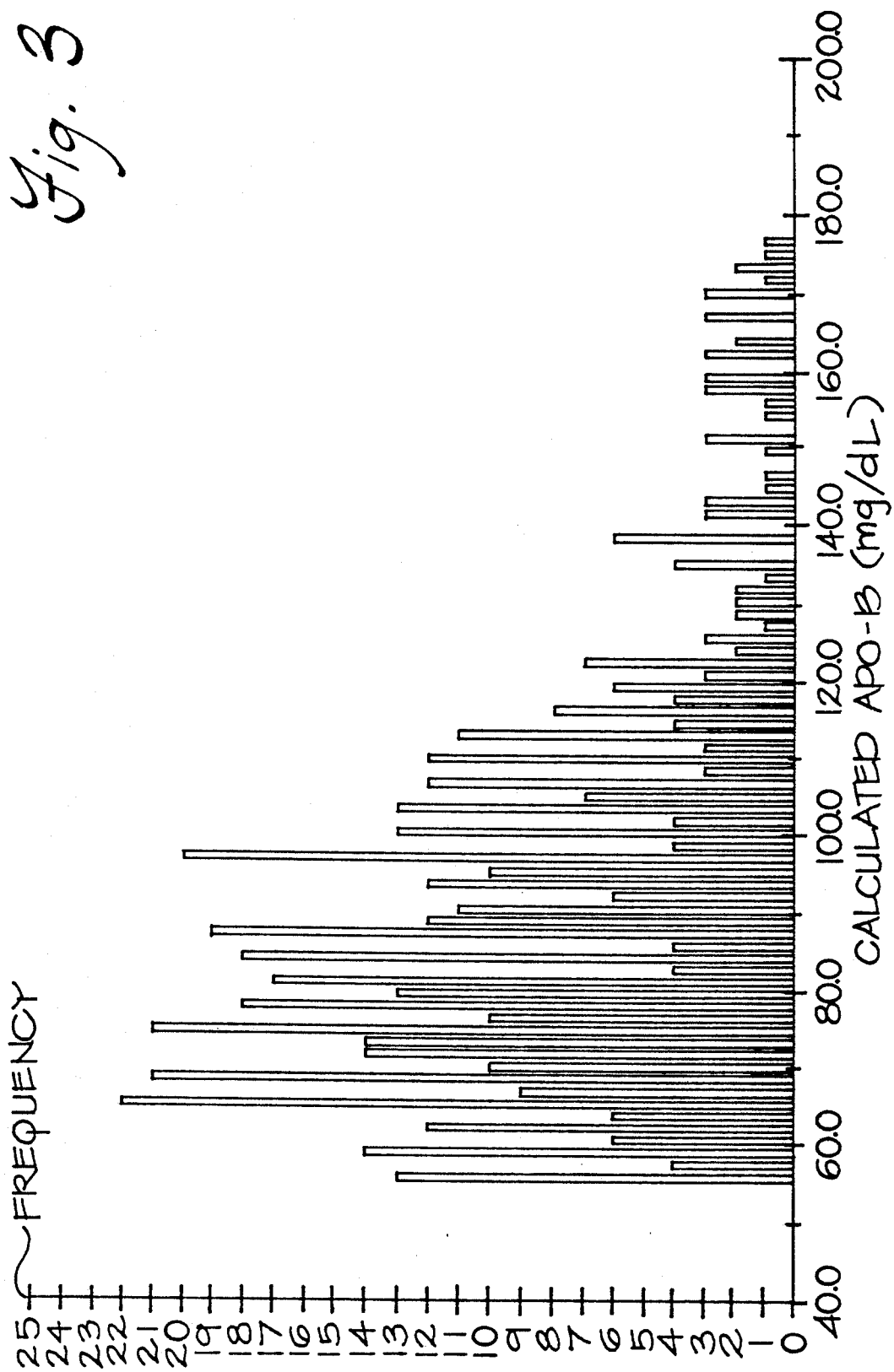
FIG. 3 demonstrates the frequency distribution of Apolipotrotein-B for a human sample population.

The frequency distribution of serum Apo-B was determined for a sample population (n=513) by the method of the present invention and is shown on FIG. 3. The sample population consisted of adolescent and adult volunteers who fasted for 12 hours. Blood specimens were obtained by venous puncture and were immediately centrifuged at 800×g for approximately 6 minutes to separate the cellular components. For each sample, an aliquot of the supernatant (serum) was combined with the preferred precipitating reagent. A precise volume of this mixture was immediately transferred to a graduated capillary tube. After the precipitation reaction came to completion (20 min), the tube was centrifuged at 800×g for six minutes. Subsequent to centrifugation, the volume of the precipitate column was read directly from the graduation marked on each tube. The precipitate column volume was equated to Apo-B concentration using the calibration curve set forth in FIG. 2. The results of these calculations as a function of the frequency of occurrence for each determination of Apo-B in the sample population are set forth in FIG. 3.

Therefore, the patient's coronary risk may be assessed by using the method of the present invention to determine Apo-B level in conjunction with the data set forth in Table 1.

While the invention has been described in connection with a preferred embodiment and representative examples, it is not intended to limit the invention to the particular form set forth, but, on the contrary, it is intended to cover alternatives, modifications, and equivalents, as may be included within the spirit and scope of the invention as defined by the appended claims.

What is claimed is:

1. A method for screening apolipoprotein B or calculated LDL cholesterol as an indicator of coronary risk in an individual comprising:
   collecting blood from an individual,
   separating the red cells from the serum in said blood,
   drawing a sample of said serum into a calibrated capillary tube,
   said capillary tube having an inner surface and an outer surface, wherein said tube contains a VLDL/LDL precipitating agent;
   contacting said serum with said precipitating agent in said capillary tube;
   agitating said serum containing capillary tube;
   allowing a VLDL/LDL precipitate to form from said serum;
   centrifuging said capillary tube;
   measuring the volume of the precipitate formed; and
   correlating said precipitate volume with known blood levels of apolipoprotein B and calculated LDL cholesterol.

2. The method of claim 1, wherein said precipitating agent is adsorbed to said inner surface of said capillary tube.

3. The method of claim 1, wherein said blood is collected from a finger-stick.

4. The method of claim 1 wherein said precipitating agent is selected from the group consisting of a high molecular weight polyanion or a polyanion and a divalent cation.

5. The method of claim 4 wherein said polyanion is selected from the group consisting of phosphotungstic acid, and sulfated polysaccharides.

6. The method of claim 5 wherein said precipitating agent is 0.01M phosphotungstic acid in 0.4M magnesium chloride with pH adjusted to 7.4 with HCl.

7. The method of claim 5 wherein said sulfated polysaccharide is selected from the group consisting of heparin, and dextran sulfate.

8. The method of claim 4 wherein said divalent cation used in combination with said polyanion is selected from the group consisting of chlorides of magnesium, manganese and calcium.

9. The method of claim 1 wherein said precipitating agent is microencapsulated.

10. A method of screening apolipoprotein B or calculated LDL cholesterol as an indicator of coronary risk in an individual, comprising
    using a standard large bore microcapillary tube to collect blood from an individual;
    separating the red cells from the serum in said blood;
    inserting a calibrated, graduated, smaller bore microcapillary tube into said large bore microcapillary tube, wherein said smaller tube contains a VLDL/LDL precipitating agent;

contacting said serum with said precipitating agent in said smaller tube by allowing capillary action to draw serum from said large bore tube into said smaller tube;

agitating said serum-containing smaller tube;

allowing a VLDL/LDL precipitate to form from said serum;

centrifuging said smaller tube;

measuring the volume of the precipitate formed; and correlating said precipitate volume with known blood levels of apolipoprotein B or calculated LDL cholesterol.

11. A method for screening apolipoprotein B or calculated LDL cholesterol as a biochemical indicator of coronary risk in a human patient comprising the steps of:

obtaining a blood serum specimen from said patient;

treating said specimen with a proportionate volume of a VLDL/LDL precipitating reagent;

vigorously agitating said treated specimen in a mixer;

allowing said agitated treated specimen to stand sufficiently to agglomerate a column of VLDL/LDL precipitate in a suspension;

measuring the volume of said column; and comparing said measurement of said column to the chart of FIG. 2 to determine the approximate amount of apolipoprotein B or calculated LDL cholesterol in said serum specimen.

12. The method of claim 11 wherein said proportionate volume is 7:1 said serum to said reagent.

13. A kit for screening apolipoprotein B or calculated LDL cholesterol as a biochemical indicator of coronary risk in a human patient comprising:

a calibrated capillary tube having an inner surface and an outer surface and containing a VLDL/LDL precipitating agent;

means for correlating the volume of a precipitate column obtained in the calibrated capillary tube to an amount of apolipoprotein B or calculated LDL cholesterol in a blood sample; and instructions to determine the amount of apolipoprotein B or calculated LDL cholesterol in a blood sample.

14. The kit of claim 13 wherein said precipitating agent is affixed to the inner surface of said capillary tube.

15. A kit for screening apolipoprotein B or LDL cholesterol as a biochemical indicator of coronary risk in a human patient comprising:

at least one (1) large bore capillary tube with cap;

at least one small bore graduated capillary tube with a cap;

at least one additional small bore graduated tube with caps, containing microcapsules of VLDL/LDL precipitating agent;

at least one sterile blood lancet;

at least one vial containing lyophilized control serum with a known amount of Apo-B (100 mg/dL or calculated LDL cholesterol (100 mg/dL); and instructions to determine the amount of apolipoprotein B or calculated LDL cholesterol in a blood sample.

16. A kit for screening apolipoprotein B or calculated LDL cholesterol as a biochemical indicator of coronary risk in a human patient comprising:

100 large bore capillary tubes with caps;

10 small bore graduated capillary tubes with caps;

100 additional small bore graduated tubes with caps, each containing microcapsules of VLDL/LDL precipitating agent prebound to their inner surface;

100 sterile blood lancets;

5 vials labeled containing lyophilized control serum with a first known amount of Apo-B or calculated LDL cholesterol;

5 vials labeled containing lyophilized control serum with a second known amount of Apo-B or calculated LDL cholesterol; and instructions to determine the amount of apolipoprotein B or calculated LDL cholesterol in a blood sample.

17. The kit of either of claims 15 or 16, wherein said precipitating agent is 0.01M phosphotungstic acid in 0.4M magnesium chloride (pH 7.4).

* * * * *